United States Patent

Gundlach et al.

Patent Number: 6,153,002
Date of Patent: Nov. 28, 2000

[54] CERAMIC MATERIAL FOR FILLINGS AND/OR DENTAL PROSTHESES AND METHOD FOR THE MANUFACTURE OF THE SAME

[76] Inventors: Hans-Werner Gundlach, Beethovenstrasse 1, D-28209 Bremen; Wolfgang Wiedemann, Am Ziegelbaum 51a, D-97204 Höchberg, both of Germany

[21] Appl. No.: 08/500,938

[22] PCT Filed: Jan. 21, 1994

[86] PCT No.: PCT/EP94/00158

§ 371 Date: Aug. 24, 1995

§ 102(e) Date: Aug. 24, 1995

[87] PCT Pub. No.: WO94/16666

PCT Pub. Date: Aug. 4, 1994

[30] Foreign Application Priority Data

Jan. 26, 1993 [DE] Germany .............................. 43 02 072

[51] Int. Cl.⁷ .......................... C04B 35/64; A61K 6/033
[52] U.S. Cl. .................. 106/35; 501/1; 423/312; 423/314; 423/315; 423/305; 264/84
[58] Field of Search .................................. 106/35; 501/1; 423/312, 314, 315, 305; 264/84

[56] References Cited

U.S. PATENT DOCUMENTS

| 4,097,935 | 7/1978 | Jarcho ........................................ 106/35 |
| 5,017,518 | 5/1991 | Hirayama et al. ........................ 106/35 |

FOREIGN PATENT DOCUMENTS 3935060  4/1991  Germany .

*Primary Examiner*—C. Melissa Koslow
*Attorney, Agent, or Firm*—Edwin D. Schindler

[57] ABSTRACT

A method is disclosed for the manufacture of a ceramic material for fillings or dental prostheses, which includes the steps of forming a precipitation product having at least one slightly soluble calcium phosphate compound, which has at least two phases of crystals; the slightly soluble calcium phosphate compound being a replacement for dental tissue. The precipitation product further includes a freely soluble compound dissolvable in the saliva of a patient's mouth and which creates a porous structure within the slightly soluble phase. The pores of this structure are filled by precipitating ions from the patient's saliva. The precipitation product is then sintered and dried, before being explosively compressed to form the ceramic dental filing material.

15 Claims, No Drawings

CERAMIC MATERIAL FOR FILLINGS AND/OR DENTAL PROSTHESES AND METHOD FOR THE MANUFACTURE OF THE SAME

DESCRIPTION

The invention concerns a ceramic material for fillings and/or dental prostheses and a method for the manufacture of such a ceramic material.

Different materials are known for the elimination of especially carious defects in the dental enamel and for the manufacture of dental prostheses, such as inlays, crowns and bridges. Widespread are amalgams, plastics and precious metals (for example gold). Each of these materials has specific disadvantages. Allergies can occur (amalgam), the mechanical properties are insufficient (plastics), or the costs are unusually high (gold).

In order to eliminate the aforementioned disadvantages, one seeks a material that is a similar as possible to natural dental enamel. Therefore, calcium phosphate compounds, especially hydroxylapatites, were developed. As concerns color and mechanical properties they closely approximate natural dental enamel. However, they have the disadvantageous characteristic that their surfaces become rough with time. With increasing fracturing of the surface, hydroxylapatite is removed more quickly (demineralisation). Although so-called bio-active hydroxylapatities were developed, which have a remineralisation property that reverses demineralisation to the greatest extent, to avoid or delay such removal, such materials have never made it past the laboratory stage. This is associated with the face that they must possess specific parameters that do not permit mass production owing to insufficient reproducibility.

On this basis, it is the object of this invention to create a ceramic material for fillings and dental prostheses that shows a reliable remineralisation behavior. It is further the object of tis invention to create a method which facilitates the simple and reliable manufacture of the ceramic material that possesses the remineralisation properties.

The ceramic material to solve this task has features owning to the formation of the ceramic material from separate phases or crystals of different materials on the one hand and the formation of a phase or crystal from an freely soluble substance, a targeted demineralisation is achieved. In the main, uniformly patterned cavities are formed in the calcium phosphate compounds that form the actual filling or the actual dental prosthesis. The calcium phosphate compounds thus receive a specific porosity. The size of the pores and the proportion of pores of the total ceramic material can be controlled by the respectively more freely soluble substance or compound. Thus a lattice is created that can be specifically predetermined as concerns its structure and free spaces. This allows conditions to be created in the ceramic material that guarantee an optimum remineralisation.

It has proven especially advantageous to select an non-stoichiometric ratio between individual phases or crystals.

Preferably the more freely soluble substances or compounds are those that are soluble in acid. The dissolving out of the corresponding crystals can thus be controlled in a targeted way through the creation of acidic conditions in the mouth, especially in the saliva. This can be promoted in that the patient has an acidic pH value or sucks a lozenge that creates an acidic pH value in the mouth.

Preferably the freely soluble substance or compound is an alpha and/or beta tribasic calcium phosphate (whitlockite, i.e., tribasic calcium phosphate in either the alpha- or beta-crystal form) or a mixture of both. This is easily formed during the manufacture of the other phase, namely the calcium phosphate compound and accommodated in the form of sorted crystals distributed evenly in the ceramic material.

Preferably crystals comprising alpha and/or beta tribasic calcium phosphate are deposited in the crystals and/or free spaces between neighboring crystals of the calcium phosphate compound. The alpha and/or beta tribasic calcium phosphate thus forms "placeholders" in the ceramic material according to this invention which after the dissolving away of the alpha and/or beta tribasic calcium phosphate cause the desired porosity.

According to a further improvement of the invention the ceramic material has a calcium deficit. Preferably this is brought about by an atomic ratio of calcium to phosphate that is less than 1.666, especially in the range between 1.580 and 1.665. This also effectively avoids the formation of mixed crystals.

A specially favorable remineralisation behavior of the ceramic material is achieved when the proportion of the alpha and/or beta tribasic calcium phosphate is 1% to 50%, especially 2% to 30% of the total weight of the ceramic material. Preferably additionally sought is an alpha and/or beta tribasic calcium phosphate and hydroxylapatite with a crystal size of 0.1 $\mu$m to 10 $\mu$m, and especially 0.5 $\mu$m to 5 $\mu$m.

A ceramic tooth filling material that serves to solve the object according to this invention, a dental cement or dental adhesive have the features wherein there is a fine-grained an/or pulverized ceramic material, as the filling substance in an artificial resin substance, in plastic and/or in a mixed or suspending agent, which is seated with calcium ions and/or phosphate ions. The artificial resin and the plastic are preferably made to be absorbable. According to which fine-grained ceramic material, is deposited as filler in a plastic or an artificial resin substance or alternatively also a mixing liquid or a suspending agent. This material can be used as hardening paste for filling, for example, cavities in the crown or enamel. It is easy to introduce in (still) pasty state in the cavity and after hardening offers a tooth filling material that is superior to pure plastic as concerns its mechanical properties. Namely it as more or less the properties of natural enamel. The same material can also be used as dental adhesive. With this material dental parts can be glued together or correspondingly modelled, for example milled filling parts can be glued in the cavity of a tooth, especially of a crown.

Preferably, the plastic for embedding the ceramic material is an absorbable plastic. For working ,this can be brought to a pasty consistence, for example, through dissolving in corresponding liquids. It is also conceivable to use insoluble plastic that retains its pasty character until after processing and only hardens after processing.

A method to solve the object according to this invention comprises the explosive compression of the dried and grained precipitation product before the subsequent sintering, a so-called basal substance being created, which after sintering has an especially favorable demineralisation and remineralisation behavior. Especially good results are shown by the explosive compression of the fine-grained precipitation products for the manufacture of the ceramic material.

Preferably the explosive compression is executed isostatically. This achieves especially uniform properties in the manufactured material. Alternatively, it is also conceivable to execute the explosive compression on one or more axes.

According to a further aspect of the invention a non-stoichiometric calcium compound is used (especially hydroxylapatite). During sintering this leads to the formation of differentiated, tat is more freely and less freely soluble phases or crystals.

According to a further proposal of the invention the precipitation product is washed at least once before drying. This simply and reliably removes undesired constituents.

According to the invention, the precipitation material is dried at more or less 200° C. Such drying can be carried out gently without the fear of negative influences on the later properties of the ceramic material. After drying, there follows according to a preferred further development of the method a maturing or verification of the crystallite of the solid and/or ground precipitation product with a expanded fluid, especially steam.

Below the invention is explained in greater detail using preferred embodiments:

The ceramic material according to this invention is used in a solid state in the dental field for dental restoration and dental prostheses, such as inlays, crowns and bridges. For this, form the blank of the ceramic material a corresponding (fixed) part is manufactured preferably by means of computer-controlled milling.

The solid ceramic material includes isolated crystals of differing substances, namely of crystals of a slightly soluble substance and deposited therein crystals of a more freely soluble substance. The slightly soluble includes mainly fluorapatite or hydroxylapatite with preferably up to 2% carbonations in the lattice. It can be modified by parts of fluorapatite, small quantities of amorphous, glass-like or polycrystalline constituents of hydrogen phosphates, pyrophosphates and/or polyphosphates.

The more freely soluble substance comprise alpha tribasic calcium phosphate or beta tribasic calcium phosphate. Alternatively, the more freely soluble substance can be formed of mixtures of alpha and beta tribasic calcium phosphate. Pure alpha and/or beta tribasic calcium phosphate can be used to form the more freely soluble substance, as well as mixtures of hydroxylapatite with alpha or beta tribasic calcium phosphate or hydroxylapatite with both alpha and beta tribasic calcium phosphate.

A ceramic material whose second, more freely soluble phase of alpha and/or beta tribasic calcium phosphate comprises 1% to 50%, especially 2% to 30% by weight has surprisingly good stability. The crystal size of both phases—that is of the more freely and ore slightly soluble substances—is preferably more or less the same, namely between 0.1 $\mu$m and 10 $\mu$m. especially 0.5 $\mu$m to 5 $\mu$m. The crystals are preferably isometric crystallites.

While pure hydroxylapatite has an atomic ratio of 1.666 calcium to phosphorus, the ceramic material according to the invention has a calcium deficit. The calcium/phosphorus atomic ration is especially 1.580 to 1.665.

A ceramic tooth filling material, a dental cement or a dental adhesive, which for working are liquid or pasty, can also be manufactured using the aforementioned ceramic material. The ceramic material serves hereby as a base for a fine-grained filling substance. For this purpose, the finished, hard material is ground. It is then mixed with a plastic. The plastic is preferably an at least partly absorbable one. The plastic is mixed with an equal or larger quantity of the ground ceramic material. It then constitutes a paste or glue.

The pasty tooth filling material is inserted in the cavity and hardens after insertion, and is namely impinged by energy, especially by light, where necessary.

Alternatively, absorbable plastics, which have been enriched with filling substances of the ceramic material, can also be left to harden to solid substances. These can serve as semifinished products for the manufacture of dental prostheses through, for example, milling.

The manufacture of the ceramic material according to this invention starts such that calcium compounds, such as calcium nitrate, are precipitated with phosphorus compounds (ammonium hydrogenphosphate) in an alkalized, aqueous base, such as sodium hydroxide, potassium hydroxide or ammonium hydroxide. Non-stoichiometric hydroxlapatite is produced as the primary precipitation product. With the corresponding reaction temperature, concentration of the components used and reaction time, precipitated, imperfect hydroxylapatite crystallites primarily grow to more or less stoichiometric hydroxylapatite. For example, the precipitation product can also be manufactured according to the method known from DE-OS 39 35 060.

Of essential importance for the invention is the order of addition of the individual substances. The ammonium hydrogenphosphate solution is accordingly slowly administered into a receiver. The receiver contains the entire quantity of calcium nitrate for reaction. Hydroxylapatite is preferably formed.

Further, the precipitation product is washed, preferably more than once, with distilled water. Preferably hot distilled water is used. It is then dried. The dry, solid precipitation product is now comminuted through grinding or use of a mortar. Preferably the precipitation product is pulverised.

Then in pressurized steam at temperatures between 100° C. and 350° C. during 1 hour up to 10 days the crystallites are matured.

According to an essential feature of the invention the pulverized precipitate product is compressed through explosive pressing together to form a basal substance, from which the finished (solid) ceramic material is sintered at temperatures of 1000° C. to 1300° C. during a period of 15 minutes to 24 hours.

Although ceramic material formed according to the method of this invention corresponds largely in appearance and physical properties to natural dental enamel, is namely whitish transparent, pigments can be added to the material to achieve the colors of individual teeth.

It is also possible to subject the ceramic material according to the invention before further processing, especially before insertion in the mouth of the patient, to an acid cure to extract the freely soluble alpha and/or beta tribasic calcium phosphate from the hydroxylapatite before the ceramic material, which comprises only hydroxylapatite, is used in the mouth of the patient. Here only newly deposited hydroxylapatite must be formed though diffusion of saliva containing calcium phosphate in to the material for a refilling of the pores in the ceramic material through the release of alpha and/or beta tribasic calcium phosphate.

What is claimed is:

1. A method for the manufacture of a ceramic material for fillings or dental prostheses, comprising the steps of:

forming a precipitation product comprising at least one slightly soluble calcium phosphate compound having at least two phases of crystals, said slightly soluble calcium phosphate compound being a replacement for dental tissue, said precipitation product further comprising a freely soluble compound dissolvable in the saliva of a patient's mouth;

drying said precipitation product;

explosively compressing said precipitation product after said drying step; and, sintering said precipitation product after said explosively compressing step.

2. The method according to claim 1, wherein said explosively compressing step is carried out isostatically.

3. The method according to claim 1, further comprising the step of washing said precipitation product at least one time prior to said drying step.

4. The method according to claim 3, wherein said washing step is carried out with hot distilled water.

5. The method according to claim 4, further comprising the step of maturing said precipitation product in pressurized steam of 100° C.–350° C. for a period of 1 hour up to 10 days, after carrying out said drying step.

6. The method according to claim 4, wherein said freely soluble compound is soluble in acid.

7. The method according to claim 4, wherein said freely soluble compound includes a tribasic calcium phosphate from the group consisting of an alpha-tribasic calcium phosphate, a beta-tribasic calcium phosphate and a combination thereof.

8. The method according to claim 7, wherein said tribasic calcium phosphate includes whitlockite.

9. The method according to claim 7, wherein said tribasic calcium phosphate is embedded in the crystals of, or free spaces between the crystals of, said slightly soluble calcium phosphate compound.

10. The method according to claim 7, wherein said tribasic calcium phosphate represents a weight ratio of 1% to 50%.

11. The method according to claim 10, wherein said tribasic calcium phosphate represents a weight ratio of 2% to 30%.

12. The method according to claim 7, wherein said tribasic calcium phosphate and the calcium phosphate compound have a crystal size of 0.1 to 10 microns.

13. The method according to claim 12, wherein said tribasic calcium phosphate and the calcium phosphate compound have a crystal size of 0.5 to 5 microns.

14. The method according to claim 11, wherein a calcium deficit exists in an atomic ratio of calcium/phosphorous of less than 1.666.

15. The method according to claim 14, wherein the atomic ratio of calcium/phosphorous is 1.580 to 1.665.

* * * * *